United States Patent [19]

Murphy

[11] Patent Number: 5,148,887

[45] Date of Patent: Sep. 22, 1992

[54] EARCUP ASSEMBLY INCORPORATING MECHANICAL ACTIVE NOISE REDUCTION

[75] Inventor: John A. Murphy, Philadelphia, Pa.

[73] Assignee: Gentex Corporation, Carbondale, Pa.

[21] Appl. No.: 678,748

[22] Filed: Apr. 1, 1991

[51] Int. Cl.⁵ .................... H04R 25/00; A42B 1/06
[52] U.S. Cl. ................... 181/129; 381/183; 2/209
[58] Field of Search .......... 181/129, 137, 138; 381/183, 187, 188; 2/209

[56] References Cited

U.S. PATENT DOCUMENTS

| 4,523,661 | 6/1985 | Scalzo et al. | 181/129 |
| 4,905,322 | 3/1990 | Aileo et al. | 181/129 X |
| 4,965,836 | 10/1990 | Andre et al. | 181/129 X |
| 5,023,955 | 6/1991 | Murphy, II et al. | 181/129 X |

Primary Examiner—L. T. Hix
Assistant Examiner—Khanh Dang
Attorney, Agent, or Firm—Shenier & O'Connor

[57] ABSTRACT

An earcup assembly for protecting the ear of the wearer from ambient sound in which a cylinder within a shell adapted to surround the wearer's ear and having a resilient seal engaging the wearer's head around his ear, receives a piston which is held in a fixed position relative to the wearer's head to maintain the volume of the space within the earcup between the piston and the ear seal opening approximately constant when the ear seal flexes under the action of ambient noise impinging on the shell.

15 Claims, 3 Drawing Sheets

EARCUP ASSEMBLY INCORPORATING MECHANICAL ACTIVE NOISE REDUCTION

FIELD OF THE INVENTION

The invention is in the field of earcups for protecting the ear of the wearer from the effects of ambient noise and, more particularly, to an earcup assembly incorporating mechanical active noise reduction.

BACKGROUND OF THE INVENTION

Various forms of sound attenuating earcups are known in the prior art for protecting the ear of the wearer from the effect of ambient noise. Most of these devices rely on the rigidity of the material making up the earcup to suppress noise. It is known that the rigidity of the material of which the earcup is formed effectively reduces relatively high frequency sound.

While sound attenuating earcups of the prior art are effective in attenuating relatively high frequency sound, they are not as effective as is desired in respect of relatively low frequency sound.

There have been developed electronic active noise reduction systems which incorporate a microphone, a feedback amplifier and a speaker. As applied to an earcup, the speaker presents the desired signal such as information or music. Noise which penetrates the earcup from the outside interferes with the desired signal. The microphone samples the combined noise and signal and supplies it to the feedback amplifier.

The feedback amplifier receives two inputs, one from the microphone and one from the input to the speaker. The feedback amplifier takes the input to the speaker and uses it to subtract the desired signal from the combined noise and signal so that after the subtraction the output of the amplifier is only the noise. This noise signal is inverted and added to the desired input to the speaker. The inverted noise portion of the speaker output then combines with and cancels the noise which penetrates the earcup. As a result, only the desired signal with no noise interference reaches the user's ear.

Electronic active noise reduction systems such as those described above are effective at low frequencies of less than 2,000 Hz. However, earcups incorporating such electronic active noise reduction systems are inordinately expensive.

SUMMARY OF THE INVENTION

One object of my invention is to provide an earcup assembly which effectively protects the ear of the wearer against ambient noise.

Another object of my invention is to provide a protective earcup assembly which is especially effective at low frequencies.

A further object of my invention is to provide a protective earcup assembly incorporating active noise reduction.

Still another object of my invention is to provide a protective earcup assembly which is relatively inexpensive for the result achieved thereby.

A still further object of my invention is to provide a protective earcup assembly which is relatively simple in construction and in operation for the result achieved thereby.

Other and further objects of my invention will appear from the following description.

BRIEF DESCRIPTION OF THE DRAWINGS

In the accompanying drawings to which reference is made in the instant specification and which are to be read in conjunction therewith and in which like reference characters are used to indicate like parts in the various views.

DESCRIPTION OF THE PREFERRED EMBODIMENT

Figure 1:
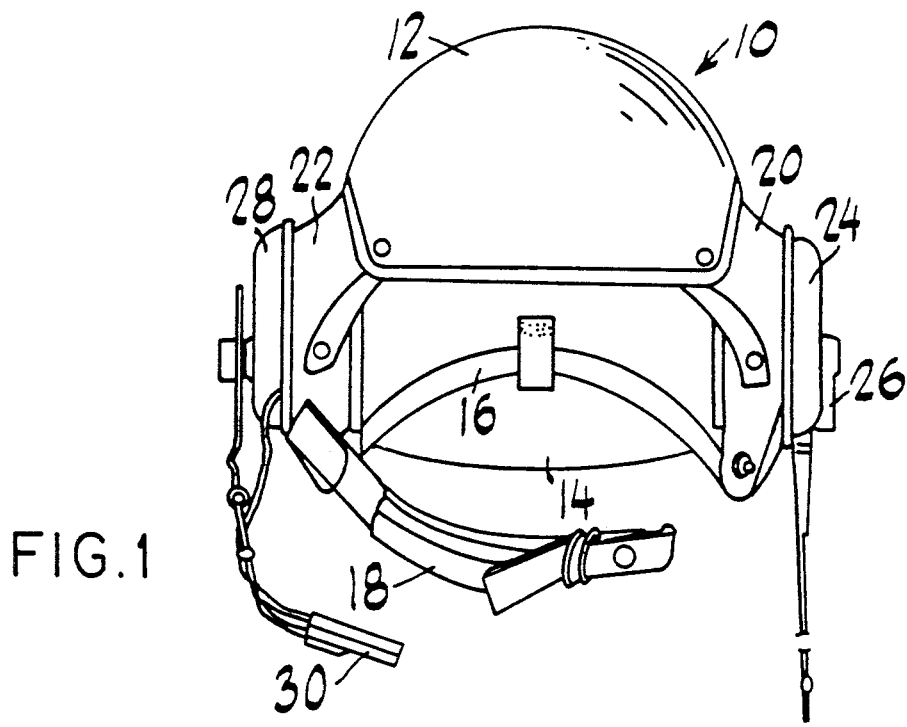
FIG. 1 is a front elevation of a helmet provided with my protective earcup assembly.

Sound attenuating earcups of the prior art incorporate a relatively rigid shell surrounding the wearer's ear. The periphery of the shell carries a resilient ear seal so supported it engages the portion of the wearer's head around his ear.

I have discovered that sound attenuating earcups of the prior art pass low frequency noise by pumping the ear seal. By "low frequency" is meant frequencies which typically are near 1,000 Hz or below. As is known, sound travels as pressure waves through the air. When these pressure waves contact an earcup, they exert a force thereon which is a function of the pressure differential between the air in the wave and the air inside the cup. This force, moreover, is a function of the area of the cup parallel to the plane of the ear seal. It will be appreciated that the force generated either presses down on or pulls out on the earcup. The earcup in turn acts on the ear seal which, as the most compliant component of the attenuating system is that which compresses or expands the most.

It will readily be appreciated that the compression and expansion of the ear seal alternately increases and decreases the volume of air inside the cup. Since the amount of air remains the same, the pressure of the air inside the cup increases and decreases with the changing volume. I have discovered that this pumping of the earcup on the ear seal is the primary cause of low frequency noise within the earcup.

Referring now to the drawings, my earcup assembly to be described more fully hereinbelow, is adapted to be incorporated in a protective helmet indicated generally by the reference character 10 having a hard shell 12 and an inner liner 14 which is provided with a nape strap 16 and a chin strap 18. Liner 14 includes respective cup supports 20 and 22 which, as is known to the art, are provided with openings in which the earcups are assembled in a manner to be described hereinbelow.

The left-hand cup support 20 carries a left-hand cup assembly 24 which may for example include an electrical switch operating arm 26. The right-hand cup support 22 carries a right-hand cup assembly 28 supporting a boom carrying a microphone 30. Both of the cup assemblies 24 and 28 may be of my protective cup construction to be described in detail hereinbelow.

Figure 2:
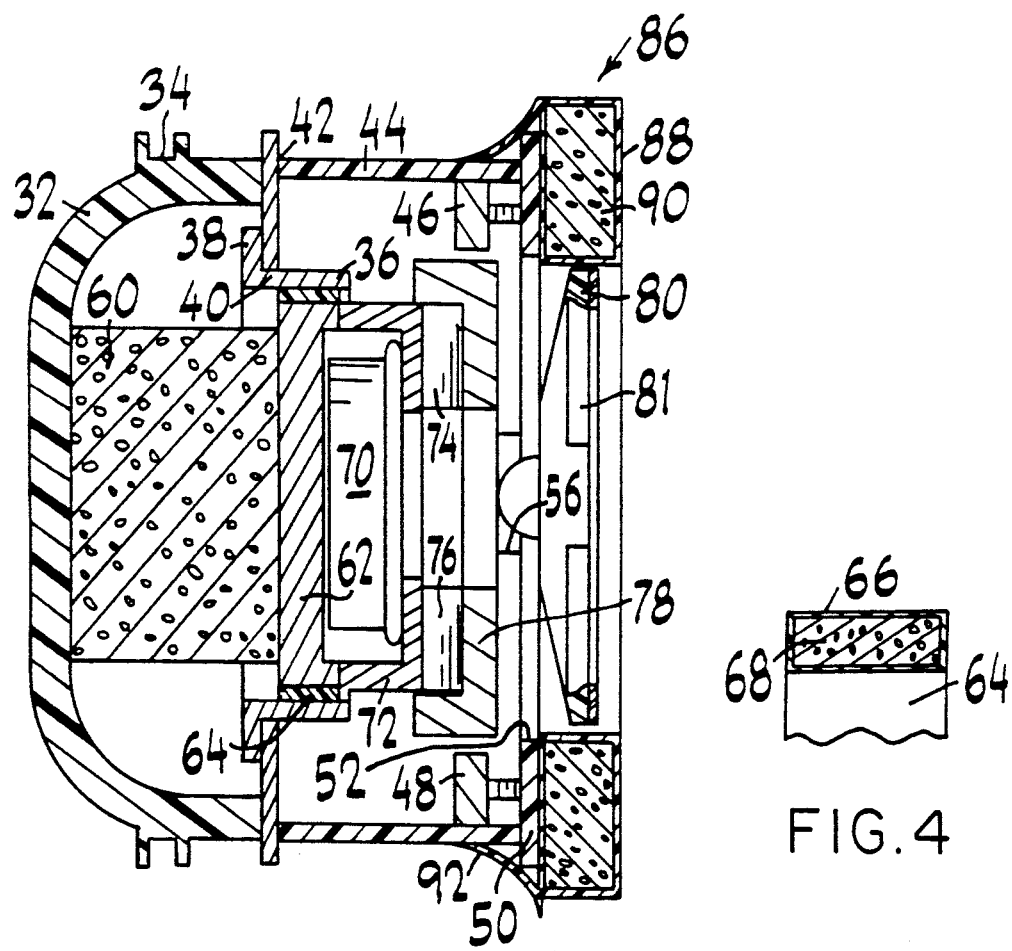
FIG. 2 is a sectional view of my protective earcup assembly.
Figure 4:
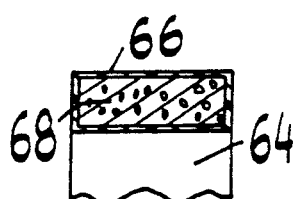
FIG. 4 is a fragmentary view illustrating the details of one element of my protective earcup assembly.
Figure 3A:
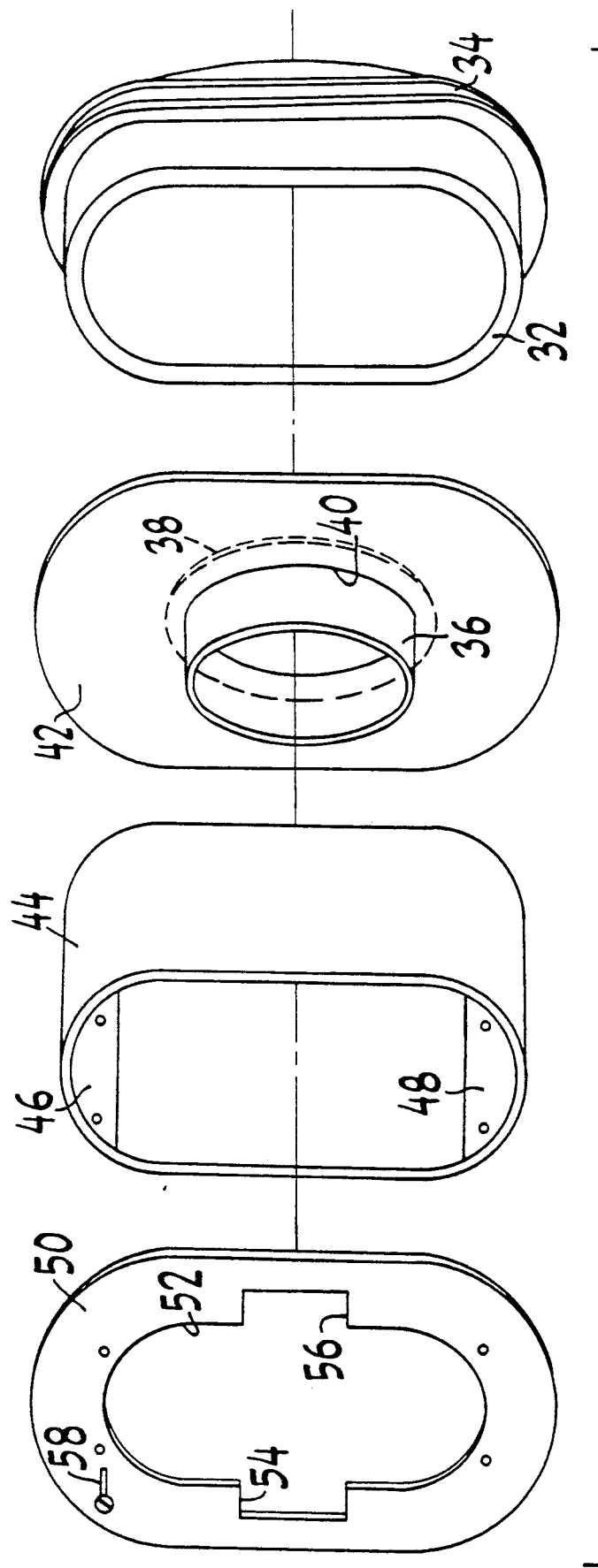
FIG. 3A is an exploded view of a first portion of my protective earcup assembly.
Figure 3B:
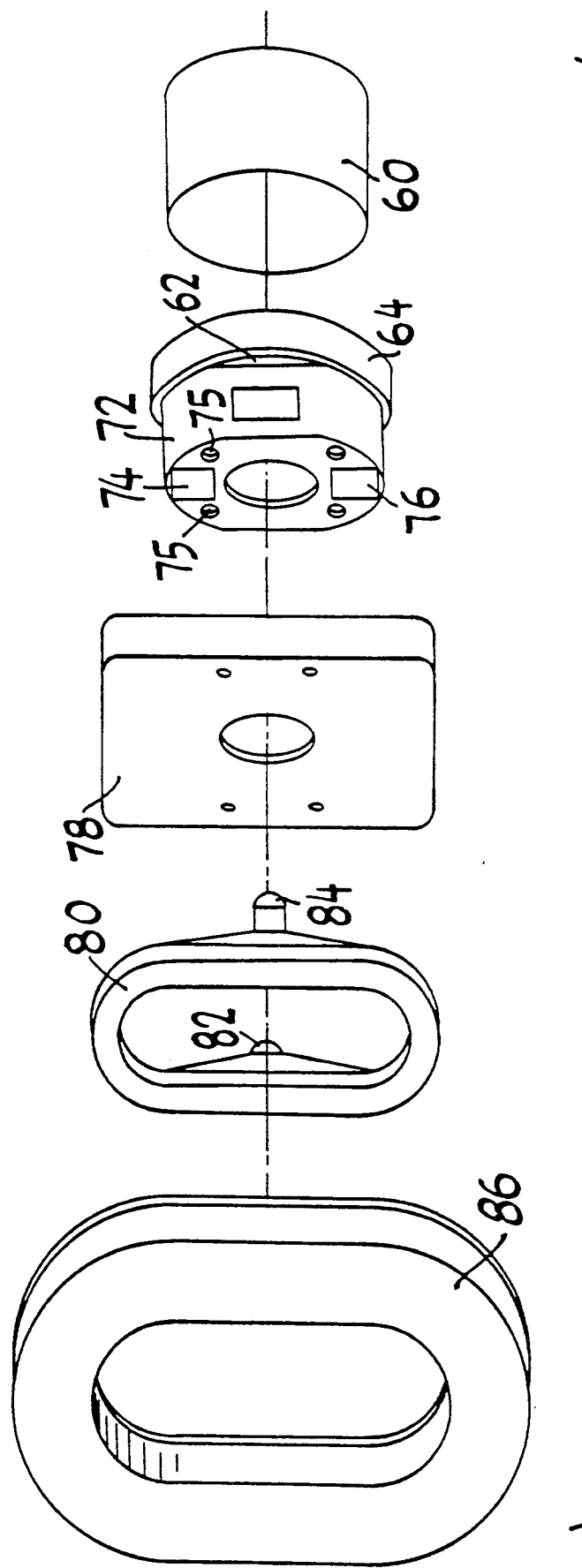
FIG. 3B is an exploded view of another portion of my protective earcup assembly.

Referring now to FIGS. 2 to 4, my assembly includes a relatively rigid earcup shell 32 formed of any suitable material, such for example as acrylontrile-butadiene-styrene copolymer. As is known in the art, the shell 32 is formed with a pair of spaced peripheral flanges forming a groove 34 which receives the opening-forming portion of one of the cup supports 20 or 22 of the linear 14, thus to support the assembly on the helmet 10. As is known in the art, when the helmet 10 is donned the earcup assemblies 24 and 28 are urged toward the wearer's head.

My assembly includes an open ended cylinder 36 machined from a suitable material such as ABS copolymer and formed with a flange 38 at the inner end thereof. An opening 40 in a support plate 42 of the same material receives the cylinder 36. I adhere the flange 38 to the plate 42 by means of any suitable adhesive, such for example as an epoxy or the like. Similarly, the plate 42 is adhered to the open end of the cup 32.

A shell extension 44 formed of a suitable relatively rigid material such as that of shell 32 is provided with a pair of webs 46 and 48 of the same material which are adhered within the extension 44. The extension 44, together with its webs 46 and 48 is secured to the plate 42 by means of an epoxy or the like.

An end plate 50 of a suitable relatively rigid synthetic resin is formed with an opening 52 having recesses 54 and 56 in the sides thereof for a reason to be explained more fully hereinbelow. I employ any suitable means, such as screws 58 for securing the end plate 50 to the blocks 46 and 48.

Cylinder 36 receives a piston 62 which is normally biased for movement out of the cup 32 and toward the wearer's ear by means of a spring 60 which may for example be a block of resilient polyurethane foam or a buildup of pads of this material. Piston 62 is formed from a suitable synthetic resin.

The periphery of piston 62 carries a seal 64 adhered to the piston by any suitable means. Seal 64 is made up of a skin 66 of 0.015" vacuum-formed polyurethane film which encloses an annular body 68 of resilient material such as polyurethane foam.

A speaker (earphone) 70 is retained on the piston 62 by means of a retainer 72 machined from aluminum. Screws 75 may be employed to secure retainer 72 to piston 62. A pair of half rollers 74 and 76 machined from a suitable material are adhered to the surface of the retainer 72 in coaxial relationship. The axes of half rollers 74 and 76 lie in one of two orthoganol axes, each normally disposed in a plane parallel to the plane of the ear seal to be described hereinbelow.

A plate 78 is machined from aluminum. It will lie in a plane parallel to the plane of the earseal, to be described hereinbelow, between the rollers 74 and 76 and the rollers attached to the foot described hereinbelow.

I vacuum-form a foot 80 having a central opening 81 from synthetic resin. A pair of half rollers 82 and 84 are cut. I cut the foot 80 as necessary to receive half rollers 82 and 84. I adhere the rollers 82 and 84 to the foot 80 in coaxial relationship with their axes normally disposed in the other of the two orthoganol axes.

My assembly includes an ear seal indicated generally by the reference character 86 made up of a skin 88 of 0.015" vacuum-formed polyurethane film and a central body 90 of resilient polyurethane foam. Ear seal 86 includes a resilient lip 92 which is stretched over the edge of the end plate 50 to retain all of the parts in assembled relationship in a manner to be described.

In the manufacture of my protective earcup assembly, existing earcups are first cut down to form the shell portion 32. The cylinder 36 and the plate 42 are machined from a suitable material, such as ABS copolymer. These parts are then glued into the cut-down cup 32. The earcup extension 44 is vacuum formed from a suitable synthetic resin and glued to the plate 42. Foam is cut to form the spring 60 and for the foam 68 of the seal 64. The skin 66 is then vacuum formed and applied to the foam 68 to form the seal 64. The foot 80 is vacuum formed and cut to the desired shape. The piston 62, retainer 72 and the rollers 74, 76, 82 and 84, are machined. The rollers 74 and 76 are adhered to the retainer 72 and the rollers 82 and 84 are adhered to the foot 80. Next the speaker retainer 72 and the piston 62 are screwed together with the speaker (earphone) 70 inside. Next the spring 60, the assembly of the piston 62 and retainer 72 and the plate 78 are loaded into the cup and the end plate 50 screwed into place. Finally, the foot 80 is positioned against plate 78 by passing the rollers 82 and 84 through the plate recesses 54 and 56 and the earseal 86 which may be of a type known to the art is applied to the end plate 50 to retain the foot in position.

When the above assembly operations are complete, the left and right earcup assemblies 24 and 28 are mounted in the openings provided in the earcup supports 20 and 22. The wearer then begins to don the helmet 10. As the earcups pass the ear, the wearer presses the bottom of the foot 80 so that the top will tilt out and the top of the ear enters the top of the foot. The earcups are then brought to the wearing position and the wearer presses his earlobes into the foot opening. Finally the helmet fit is adjusted.

From the foregoing, it will be appreciated that the cylinder 36 is rigidly attached to the earcup made up of the shell 32 and the extension 44. Moreover, the plate 42 effectively cuts the earcup into two separate chambers, one of which is to the right of the plate 42 as viewed in FIG. 2 and the other one of which is to the left.

In use of the device, the foot 80 rests against the wearer's head around his ear within the opening of the ear seal 86. Through the medium of the rollers 82 and 84, plate 78 and retainer 72, the piston is held in position with reference to the wearer's head.

In response to forces of vibration applied to the cup 32, the cup may move inwardly relative to the wearer's head compressing the ear seal 86 to reduce the volume of the chamber to the right of the plate 42. Conversely, if the cup tends to move outwardly this volume tends to increase. As the cup moves inwardly, piston 62 moves relatively outwardly with reference to the chamber. Since the area of the piston is approximately the same as that of the ear seal opening, the volume remains substantially constant. Since the volume of the chamber to the right of the plate 42 remains constant, there can be no compression or expansion of air in this chamber with the result that no noise is transmitted to the ear.

As has been explained hereinabove, the foot 80 must stay flat against the head. When the cup tends to tilt relative to the plane of the foot, the assembly of the plate 78 and the pairs of rollers 82 and 84 and 74 and 76 act as a universal to prevent the line of drive from the piston to the rollers to the foot from being disconnected when the cup pitches relative to the foot.

It will be seen that I have accomplished the objects of my invention. I have provided a protective earcup assembly which effectively protects the ear of the wearer against ambient noise. My earcup assembly is especially effective at low frequencies. It incorporates active noise reduction. It is relatively inexpensive for the results achieved thereby. It is simple in construction and in operation.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. An earcup assembly for protecting an ear of a wearer's head from ambient noise including in combination a relatively rigid shell adapted to surround the ear of a wearer and to enclose a space adapted to communicate with the wearer's ear, said space occupying a volume, a resilient seal carried by said shell and having an opening to permit said seal to engage the wearer's head around the ear, a compensating element communicating with said space, means mounting said compensating element on said shell for movement relative to said shell in directions into said space and out of said space, and means responsive to flexing of said seal in response to ambient noise for moving said compensating element to maintain the volume of said space relatively constant.

2. An assembly as in claim 1 in which said means for maintaining said volume constant comprises a displaceable element, means mounting said displaceable element on said shell for movement relative thereto and means responsive to movement of said shell relative to the wearer's head for so moving said element relative to said shell as to maintain said volume substantially constant.

3. An assembly as in claim 2 in which said means for moving said element relative to said shell comprises means for holding said element in a fixed position relative to the wearer's head.

4. An assembly as in claim 1 in which said means mounting said element comprises means forming a cylinder in the interior of said shell to form a chamber adjacent to the ear of the wearer, said element comprising a piston disposed in said cylinder whereby said chamber forms said space and in which said means for moving said element comprises means for holding said piston in a fixed position with reference to the head of the wearer.

5. An assembly as in claim 4 in which said seal has an opening of a predetermined size, said piston having a face, the face of said piston having a size approximately that of said opening.

6. An assembly as in claim 4 in which said means for holding said piston in said fixed position comprises means adapted to urge said piston towards the wearer's head and means including a foot adapted to engage the wearer's head for acting against said urging means.

7. An assembly as in claim 6 in which said foot has an opening for receiving the ear of the wearer, said foot adopted to engage the head of the wearer around the ear within the opening of said seal.

8. An assembly as in claim 7 including means forming a universal joint coupling said foot to said piston.

9. An earcup assembly for protecting an ear of a wearer's head from ambient noise including in combination a shell-like first member adapted to surround the ear of the wearer, a second member, means including means mounting said second member on said first member to enclose a space adapted to communicate with the ear of the wearer, said space occupying a volume, said mounting means mounting said second member for movement relative to the first member in directions into and out of said space, means adapted to hold one of said first and second members in a fixed position relative to the wearer's head, and a resilient seal adapted to fit between the other of said first and second members and the wearer's head, the arrangement being such that said second member moves relative to said first member as said seal flexes in response to ambient noise thus to maintain the volume of said space substantially constant.

10. An assembly as in claim 9 in which said holding means holds said second member in said fixed position and in which said resilient seal is carried by said first member.

11. An earcup assembly for protecting an ear of a wearer's head from ambient noise including in combination an earcup adapted to surround the ear of the wearer's head, a resilient seal carried by said earcup and having an opening for permitting said seal to engage the head of the wearer around the ear, means forming a cylinder within said earcup, said cylinder having an end adapted to open toward the ear of the wearer, a piston mounted for movement in said cylinder, said piston and said cylinder forming means forming a space within said earcup adapted to open toward the wearer's ear, said space occupying a volume, means adapted to bias said piston toward the wearer's ear, a foot adapted to receive the ear of the wearer and adapted to engage the wearer's head around the ear within the seal opening and means connecting said foot to said piston so as to be adapted to hold said piston in a fixed position relative to the wearer's head whereby flexure of said seal in response to ambient noise impinging on said earcup moves said piston relative to said earcup to maintain the volume of said space relatively constant.

12. An assembly as in claim 11 including an acoustic transducer carried by said piston.

13. An assembly as in claim 11 in which said piston face has an area approximately equal to that of said ear seal opening.

14. An assembly as in claim 11 in which said connecting means comprises a universal joint.

15. An assembly as in claim 14 in which said universal joint comprises first roller means on said foot, said first roller means being rotatable around a first one of a pair of orthogonal axes, a plate engaged by said first roller means, second roller means on said plate, said second roller means being rotatable around the other of said orthoganol axes, said second roller means engaging said piston.

* * * * *